United States Patent [19]

Simon et al.

[11] 4,309,185
[45] Jan. 5, 1982

[54] CHEMICAL ANALYSIS FOR QUALITY DETERMINATION OF TUNA

[75] Inventors: Frank J. Simon, San Marcos; Wilfred B. Slater, Carlsbad, both of Calif.

[73] Assignee: Ralston Purina Company, St. Louis, Mo.

[21] Appl. No.: 11,241

[22] Filed: Feb. 12, 1979

[51] Int. Cl.³ ............................................. G01N 33/12
[52] U.S. Cl. ................................. 23/230 R; 23/230 B; 426/231
[58] Field of Search ........................ 23/230 R, 230 B; 426/231, 643

[56] References Cited

U.S. PATENT DOCUMENTS 3,851,078 11/1974 Khayat et al. ................... 426/643 X
4,105,800 8/1978 Jahns et al. ...................... 426/231 X

OTHER PUBLICATIONS

Tokunaga, "Trimethylamine Oxide and its Decomposition in the Bloody Muscle of Fish", Chem. Abstr. No. 86698a, vol. 73, 1970.
Yamagata et al., "Accuracy of Predicting Occurrence of Greening of Tuna Based on Content of Trimethylamine Oxide", Chem. Abstr. No. 98293y, col. 74, 1971.
Boland et al., "Collaborative Study of a Method for the Determination of Trimethylamine Nitrogen in Fish", Chem. Abstr. No. 18691j, vol. 75, 1971.
Tokunaga et al., "Quality Evaluation of Canned Marine Products I. Determination of the Ratio of DMA to TMA in Canned Albacore",Chem. Abstr. No. 95041q, col. 83, 1975.
Mendes et al., "Change of Total Volatile Bases and Trimethylamine in Fish and their use as Indicator of Quality", Chem. Abstr., vol. 85, 1976.

*Primary Examiner*—Arnold Turk
*Attorney, Agent, or Firm*—W. Dennis Drehkoff

[57] ABSTRACT

Method of determining the quality of fish prior to processing and packaging thereof which comprises measuring the quantitative distribution of trimethylamine in the fish and more particularly, the extent of migration of trimethylamine from dark to light meat in the fish.

4 Claims, 3 Drawing Figures

CHEMICAL ANALYSIS FOR QUALITY DETERMINATION OF TUNA

BACKGROUND OF THE INVENTION

The instant invention generally relates to a method of determining the quality of fish and more specifically, to a method to determine the quantitative distribution and rate of migration of trimethylamine in fish.

This invention was conceived and developed largely for tuna and tuna-like species because of the special problems encountered with the preservation of both the dark and light meat present therein. Therefore, it will be explained largely with respect to tuna and tuna-like species, although it can be used for other types of fish, i.e., haddock, cod, pollack, cusk and hake, in the broader aspects of the invention.

Tuna and tuna-like fish, most often, are caught in the ocean many miles from port. The fish are then placed into a brine solution in holds in the fishing vessel and subsequently frozen when the holds are filled. The freezing may occur within a matter of a few hours or days, depending upon the availability of fish. The tuna may deteriorate if not frozen quickly or thoroughly or if exposed to air for long periods of time. The quality of fish is determined by organoleptic evaluation after they have thawed and on the production line prior to canning.

Organoleptic methods of analyzing tuna fish have been accepted as the standard in the industry for determining the quality of tuna fish prior to precooking in the canning process. These methods include the evaluation of individual tuna fish for rancid or putrid odors, discoloration, soft mushy skin, bent or deformed carcasses and other indicators of bacterial contamination which can be recognized by the human senses. In the present practice of this conventional process, a skilled worker doesn't have many problems in determining high quality and low quality fish. However, it is virtually impossible for the worker to discover a fish of marginal quality, or one that is about to become low quality. Additionally, many fish are often discarded because of a bent, deformed or mangled carcass even though the quality of the meat may be very high.

It's been recognized in the industry that the presence of amines in fish is related to the deterioration thereof. For example, in an article entitled, "Assessment of Green Tuna: Determining Trimethylamine Oxide and its Distribution in Tuna Muscles", by M. Yamagata et al, appearing in *Journal of Food Science*, Vol. 34, p. 156, (1969), it is stated that the off-color "greening" condition of pre-cooked tuna is very closely related to the trimethylamine oxide content of the raw meat.

In another article entitled, "Production of Dimethylamine In Muscle of Several Species of Gadoid Fish during Frozen Storage, Especially In Relation To Presence Of Dark Muscle" by C. H. Castell et al, appearing in the *Journal of The Fisheries Research Board of Canada*, Vol. 28, No. 1, January 1971, it is stated that dimethylamine was produced in the muscle of five gadoid species during storage at $-5°$ C. When the dark lateral muscle was removed prior to freezing, the production of the dimethylene was either greatly inhibited or reduced. A further article by T. Tokunaga entitled, "Trimethylamine Oxide And Its Decomposition In The Dark Muscle Of Fish," in the Bulletin of the *Japanese Society of Scientific Fisheries*, Vol. 36, No. 5, p. 510 (1970) expresses a similar view. In that publication, it was reported that dark and light muscles of different species of fish were kept separately but under similar conditions in order to examine changes in content of trimethylamine, dimethylamine and formaldehyde during storage for 25 days at $0°$ C. No change occurred, but a fairly rapid increase in amines was observed in the dark muscle of all the samples. At $-6°$ C., trimethylamine content was somewhat less than that produced at $0°$ C., but dimethylamine slowly increased. The formation of the amines in the dark muscle was considered to be caused by enzymatic action and was thought to be used as in index to fish freshness prior to spoilage by bacterial growth.

However, there is a need for a method to chemically analyze the quality of fish prior to processing and particularly to identify the rate and extent of migration of trimethylamine from dark to light meat in fish to detect low quality fish that may pass organoleptic evaluation.

BRIEF SUMMARY OF THE INVENTION

It is a principal object of the present invention to provide a method to determine the quality of fish.

Another object of the present invention is to provide a method of determining the quality of tuna fish by chemical analysis.

And yet another object of the present invention is to provide a method to show the migration of trimethylamine from dark to light meat in fish and the chemical analysis thereof to determine the quality of the fish.

One further object of the invention is to provide a method to determine the ratio of trimethylamine in the dark and white meat of tuna and thereby provide the quality of the fish thereof.

Briefly, the present invention provides a method for determining the quality of fish which comprises measuring the rate and extent of migration of trimethylamine from dark to light meat.

DETAILED DISCUSSION OF THE INVENTION

Trimethylamine is a reduction product of trimethylamine oxide, which is found in the dark muscle of fish. Trimethylamine oxide is a product of the digestive processes of fish and helps in the buoyancy control of the fish. Other degradation products of trimethylamine oxide include dimethylamine and formaldehyde. As previously discussed, the presence of large amounts of trimethylamine oxide in the white muscle of tuna fish is indicative of a "greening" effect and renders the meat undesirable. Trimethylamine is generated from bacterial action on protein and trimethylamine oxide in fish. The time period between the death of the fish and freezing conditions to stop the bacterial or enzymatic action on trimethylamine oxide is when the trimethylamine migrates from the red or dark meat to the white or light meat areas. When fish are frozen, trimethylamine is a liquid with low vapor pressure, and above the freezing point of water, trimethylamine is gaseous with high vapor pressure. It appears to be a natural freeze-thaw indicator and migrates when it is in the gaseous state. The distribution of other degradation products of trimethylamine oxide, such as dimethylamine and formaldehyde into the white muscle of fish has not been shown to produce undesirable effects of a substantial nature to fish. The distribution of trimethylamine, however, has been shown in deteriorated fish. This distribution, if postured in a ratio form, may be used to re-evaluate the quality of marginal fish which may have passed organoleptic evaluation or may be used to re-evaluate fish which have not passed organoleptic evaluation due to physical distortions, i.e., bent, mangled form, of the fish but yet retains good quality meat. By using the chemical analysis of the instant invention, improvement in processing yields can be gained by the evaluation of bent, mangled fish to more definitely determine its rating: "prime", "commercial", "marginal", or "reject"; regardless of its organoleptic evaluation. Bent, mangled fish are routinely graded "reject" by organoleptic evaluation. A random sampling of organoleptically graded "marginal" fish subjected to the chemical analysis of the instant invention may show the fish to be improperly graded and if the chemical analysis determines the grade to be "commercial" or "prime", further improved processing yields can be obtained.

Figure 1:
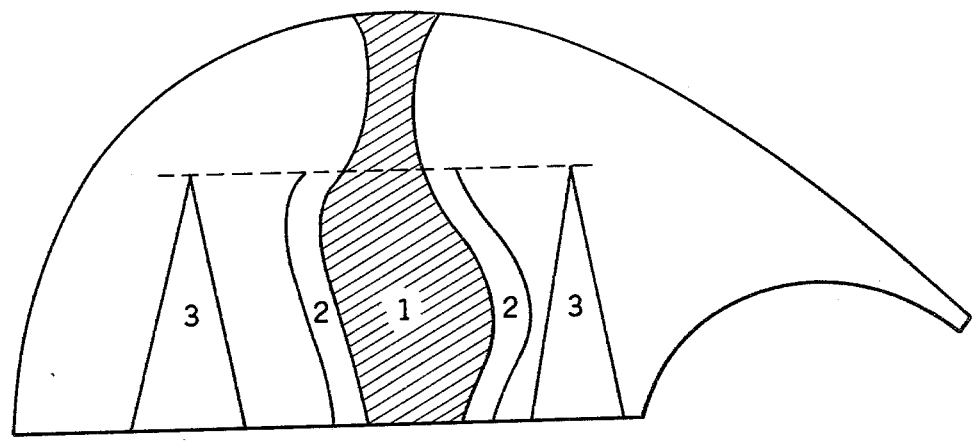
FIG. 1 represents one-half cross section of a species of tuna, showing dark and light meat.

In accordance with the present invention, it has been determined that the trimethylamine migrates from red or dark meat to white or light meat. The initial rate of reduction of trimethylamine in the red meat and the initial rate of increase of trimethylamine in the white meat has the ratio of 5:1. This is the ratio of white to red meat. Since the migration of trimethylamine from red meat to white meat is the indication of the spoilage of the meat, a ratio lower than 5:1, when corrected for the mass of the fish, would indicate fish that should be graded "reject" and not subjected to further processing and canning. FIG. 1 shows a one-half cross section of a species of tuna. The shaded area identified as 1 shows the dark or red meat running vertically through the cross section. The areas labeled 2 and 3 in FIG. 1 are the light meat areas into which the trimethylamine migrates to when the fish is stored under improper conditions, i.e., inadequate or delayed refrigeration. One method for determining the trimethylamine content in fish is shown by W. J. Dyer in the Journal of the AOAC (Vol. 42, No. 2, 1959) *Report On Trimethylamine In Fish*. The following comprises the method.

Method of Determining Trimethylamine In Fish

The following reagents are required for the analyses.
(a) Trichloroacetic acid—7.5% aqueous solution.
(b) Toluene—Reagent grade, dried over anhydrous $Na_2SO_4$. To remove interferences, shake with 1 N $H_2SO_4$, distill, and dry with anhydrous $Na_2SO_4$.
(c) Picric acid—Stock solution: dissolve 2 g dry picric acid, reagent grade, in 100 ml moisture-free toluene. Working solution: Dilute 1 ml to 100 ml with moisture-free toluene.
(d) Potassium hydroxide solution—Dissolve 100 g 25% KOH in 100 g water.
(e) Formaldehyde—Dilute 10 ml formalin (40% formaldehyde, commercial, shaken with magnesium carbonate, and filtered) to 100 ml with water.
(f) Trimethylamine standard solution—Stock solution: Add 0.682 g trimethylamine hydrochloride to 1 ml HCl and dilute to 100 ml with water. Check basic nitrogen content of 5 ml aliquots by adding alkali and distilling into standard acid in a micro-Kjeldahl distillation apparatus. This solution is quite stable. Dilute standard: add 1 ml to 1 ml HCl and dilute to 100 ml with water.

Determination (a) Extraction—Weigh 100 g minced or chopped, well mixed sample of fish or fillet. Add 200 ml 7.5% trichloroacetic acid, and blend, or if more convenient, shake occasionally over a period of several hours. (The mixture is stable and often is used without filtration.

(b) Colorimetric estimation—Pipet and aliquot (preferably containing 0.01–0.03 mg trimethylamine nitrogen) into a 20×150 mm pyrex test tube. For trimethylamine values (mg N per 100 g) in the range 1–5 use 1 ml extract and dilute with water to 4.0 ml. Add 1 ml HCHO reagent, 10 ml toluene from an automatic pipet, and 3 ml $K_2CO_3$ solution. Stopper the tube with a polyethylene stopper and shake vigorously by hand about 40 times. Pipet off 5 ml of the toluene layer into a small test tube containing about 0.3 g anhydrous granular $Na_2SO_4$. Avoid removing droplets of the aqueous layer. Stopper the tube with a polyethylene stopper and shake gently a few times to dry the toluene. Decant into a dry colorimeter tube. Add 5 ml picric acid reagent and mix by swirling gently. Read in a colorimeter, using a filter with maximum transmittance at 410 m$\mu$ against a blank carried through the procedure. The color is stable.

It is apparent that "prime" or "commercial" grade fish sometimes look very poor and are down graded by the cannery worker using organoleptic evaluations. In an effort to correlate the chemical analysis of the present invention with organoleptic analysis the following examples were undertaken to show the present invention by way of illustration and not limitation.

EXAMPLE 1

Figure 2:
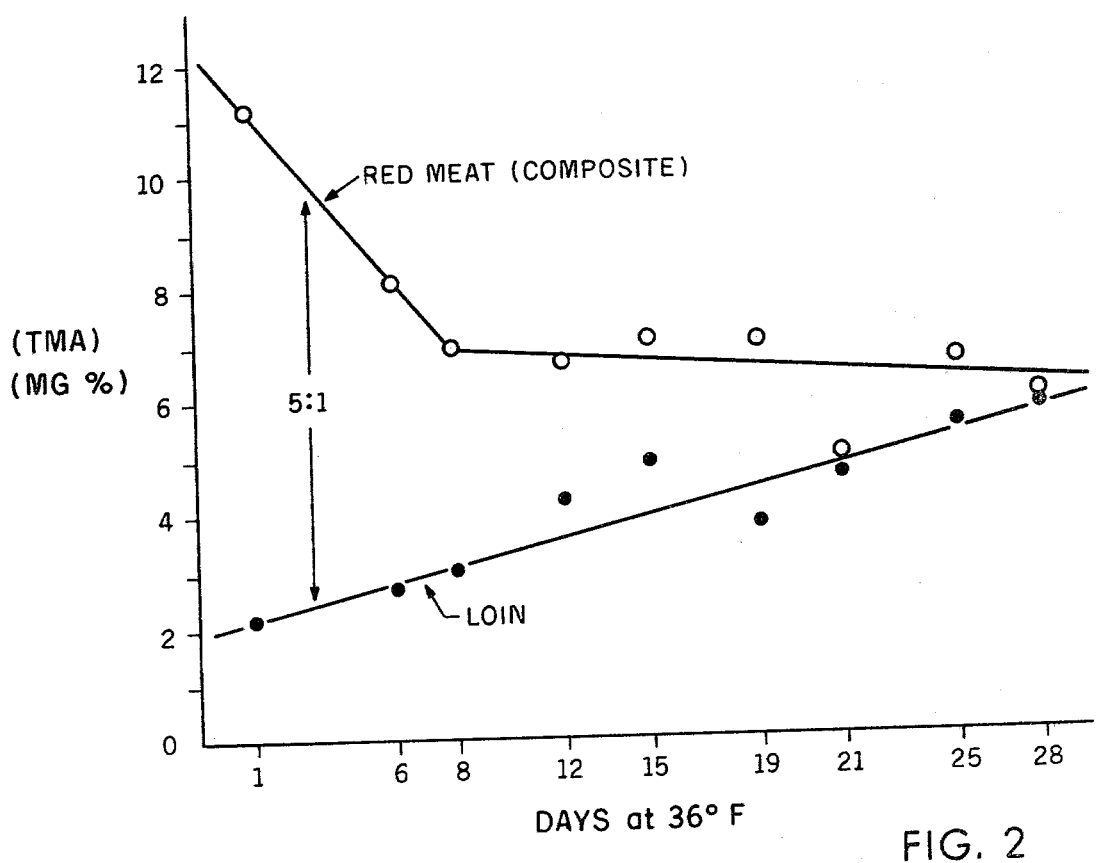
FIG. 2 graphically represents the migration of trimethylamine from dark or red meat to light or white meat of tuna.

Twelve groups of prime yellowfin tuna were frozen to −15° F. and subsequentially two fish from each group were removed from the freezer in 2 to 3 day intervals and placed in another freezer at 36° F. This procedure at the end of a 1 month period of time produced fish that were at 36° F. for increasing periods of time. After 30 days, the fish were butchered, composited and samples were prepared for analysis. The meat was subjected to the chemical analysis previously described in the specification and it was found that as the trimethylamine concentration in red meat declined, it increased in the white meat confirming the migration phenomenon. FIG. 2 graphically represents the results of the experiment showing the concentration of trimethylamine in milligrams percent in one ordinate and the other showing the age of the sample at 36° F. It is noted that the initial rate of the slope on the FIG. 2, or the reduction of trimethylamine in the red meat and the initial rate of increase of trimethylamine in the white meat has the ratio of 5:1. As previously recited, this is the ratio of white to red meat also.

EXAMPLE II

Samples of yellowfin tuna were taken in accordance with the half cross section of a whole fish depicted in FIG. 1. Samples were taken from three places: red meat from the area labeled 1, white meat from the area labeled 3, and also white or light meat taken from the intermediate zone labeled 2. The samples were subjected to the chemical analysis previously described in the specification. The following table shows that the red meat samples have the highest values, the loins have the lowest and loin portions adjacent to the red meat area have an intermediate trimethylamine concentration. In this experiment, portions of cross sections of the fish were utilized rather than whole fish composites as shown in Example 1. The following table shows the amount of trimethylamine obtained from each sample area relative to the age of the sample at 36° F.

| | TRIMETHYLAMINE CONTENT | | |
|---|---|---|---|
| Day # | Sample 1 | Sample 2 | Sample 3 |
| 0 | 4.8 MG/C | 2.3 MG/C | 1.1 MG/C |
| 1 | 4.6 | 2.7 | 1.3 |
| 4 | 8.7 | 5.1 | 1.5 |
| 8 | 7.5 | 5.1 | 2.7 |
| 11 | 5.4 | 3.6 | 1.8 |
| 18 | 7.5 | 5.7 | 4.8 |
| 25 | 6.3 | 5.4 | 4.5 |
| 35 | 5.4 | 5.4 | 4.5 |

Figure 3:
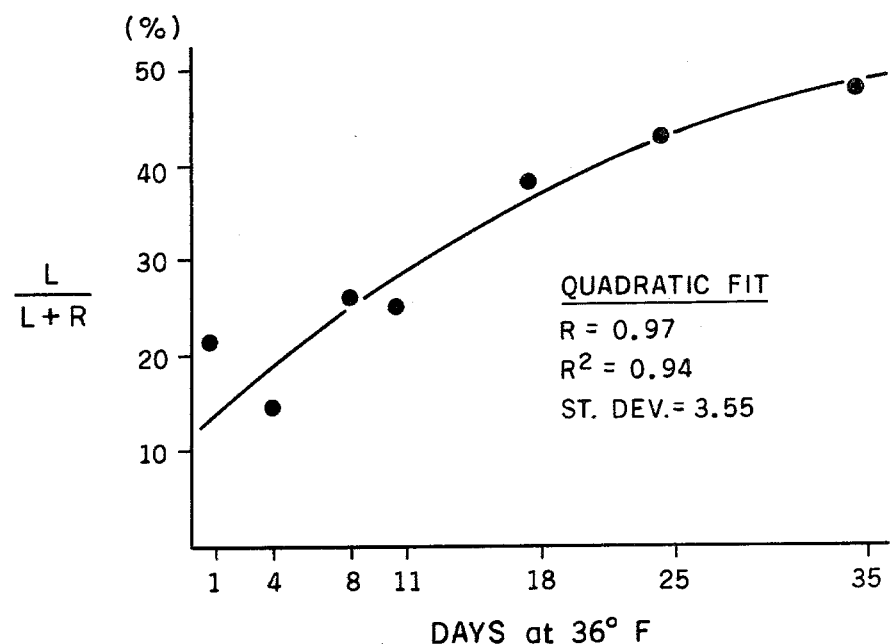
FIG. 3 graphically represents a correlation of the value of trimethylamine in loins over the loin plus red meat, corrected for the amount of trimethylamine in the total mass of yellowfin tuna.

A good correlation is obtained by using the value of trimethylamine in loins over the loin plus red meat, which takes into account the amount of trimethylamine in the total mass of the fish. Values were obtained using quandratic curve fits for a correlation coeifficient of $R=0.97$, $R^2=0.94$, with a standard deviation of the estimate being 3.55. This infers that one can predict storage of the fish to the nearest 3.5 days based on the chemical evaluation. FIG. 3 graphically represents this correlation.

EXAMPLE III

This example compares organoleptically graded fish that were then submitted for chemical analysis. Random samples of yellowfin tuna were obtained over periods of 1 month in accordance with the procedure described in Example 1. The samples were submitted for chemical analysis as previously described. The fish were then processed, canned and organoleptically graded by an experienced panel of three members. The following table shows the organoleptic grades that were given to the fish and the ratio of trimethylamine in loin over loin plus red meat.

$\frac{L}{L+R}$ vs. ORGANOLEPTIC EVALUATION OF CANNED PRODUCT

| Days at 36° F. | $\frac{L}{L+R}$ | Organoleptic Evaluation |
|---|---|---|
| 1 | 15.9% | Dry, Good Color, Good Taste, Good Odor |
| 6 | 25.0% | Soft, Tender, Good Color, Taste, Odor |
| 8 | 30.3% | Dry, Chewy, Bland Taste, Low Aroma |
| 12 | 38.9% | Chaulky, Not Pink, Terrible Aftertaste, O.K. Odor |
| 15 | 41.0% | Soft, Pink, Stale Odor, Bad Aftertaste |
| 19 | (34.3%) | Sour & Stale - Pink |
| 21 | 48.4% | Sour & Stale |
| 25 | 45.0% | Woody, Sour |
| 28 | 54.1% | Woody, Sour |

It is evident that in almost every case the organoleptic evaluation agrees with the trimethylamine migration calculation with one exception: This exception, at 19 days, shows a sampling or analytical error. The table also shows that when the ratio of trimethylamine in loin over loin plus red meat is above about 31% concentration, (in this sample, 30.3%), the meat is characterized in terms by the test panel that would subject it to a "reject" grade. Thus, if fish contained a lower ratio of trimethylamine and appeared to be bent, mangled or mutilated and received a "reject" grade by the organoleptic evaluator, it may still be used in further processing.

It can be seen that when the ratio $$\frac{L}{L+R}$$

wherein L=the amount of trimethylamine in the loin portion, and R=the amount of trimethylamine in red meat equals above about 31% concentration, a minimum acceptable level of trimethylamine is present in the fish. Amounts higher than this would indicate "reject" grade fish regardless of other physical characteristics judged organoleptically. The ratio is corrected for the trimethylamine content in the total mass of the fish. It is an adequate and sufficient indicator of poor quality fish and indicates spoilage of fish.

The above Examples are merely illustrative of the instant invention and it will be understood that various other details, ingredients or processes which have been described may be made without departing from the spirit of the instant disclosure, and such changes and other modifications are intended to be included within the scope of the instant disclosure and appended claims.

What is claimed is:

1. A method of determining the spoilage of fish comprising measuring the quantitative distribution of trimethylamine from the dark meat to the light meat of fish, placing the results of said measurement in the form of a ratio of the amount of trimethylamine in dark meat to the amount of trimethylamine in light meat, which is corrected for the total mass of the fish, said ratio $$\frac{L}{L+R,}$$

wherein L equals the amount of trimethylamine in the white or light meat of the fish and R equals the amount of trimethylamine in the red or dark meat of fish.

2. The method of claim 1 wherein the spoilage of fish is measured by chemical analysis.

3. The method of claim 1 wherein the spoilage of fish is when the ratio $$\frac{L}{L+R}$$

is above about 31%.

4. A method of determining the spoilage of tuna and tuna like fish comprising measuring the migration of trimethylamine from the dark meat to the light meat of the fish by chemical analysis, placing the results of said measurement in the form of a ratio of the amount of trimethylamine in dark meat to the amount of trimethylamine in light meat, which is corrected for the total mass of the fish, said ratio being $$\frac{L}{L + R}$$

wherein L equals the amount of trimethylamine in the white or light meat of the fish and R equals the amount of trimethylamine in the red or dark meat of the fish, and spoilage of the fish being indicated when said ratio is above about 31%.

* * * * *